（12）United States Patent
Yoo et al.

(10) Patent No.: US 11,786,710 B2
(45) Date of Patent: Oct. 17, 2023

(54) SKULL IMPLANT-TYPE AUTOMATIC FLUID DRAIN DEVICE (71) Applicants: National Cancer Center, Gyeonggi-do (KR); Eulji University Industry Academy Cooperation Foundation, Gyeonggi-do (KR)

(72) Inventors: Heon Yoo, Seoul (KR); Kwang Gi Kim, Seoul (KR); Young Tae Kim, Incheon (KR); Seung Hoon Lee, Daejeon (KR)

(73) Assignees: National Cancer Center, Gyeonggi-do (KR); Eulji University Industry Academy Cooperation Foundation, Gyeonggi-do (KR)

( * ) Notice: Subject to any disclaimer, the term of this patent is extended or adjusted under 35 U.S.C. 154(b) by 941 days.

(21) Appl. No.: 16/608,223

(22) PCT Filed: Apr. 24, 2018

(86) PCT No.: PCT/KR2018/004742
§ 371 (c)(1),
(2) Date: Oct. 25, 2019

(87) PCT Pub. No.: WO2018/199592
PCT Pub. Date: Nov. 1, 2018

(65) Prior Publication Data
US 2021/0100990 A1 Apr. 8, 2021

(30) Foreign Application Priority Data
Apr. 26, 2017 (KR) .................. 10-2017-0053600

(51) Int. Cl.
*A61M 27/00* (2006.01)
*A61M 39/02* (2006.01)

(52) U.S. Cl.
CPC ...... *A61M 27/006* (2013.01); *A61M 39/0247* (2013.01); *A61M 2039/0276* (2013.01); *A61M 2210/0687* (2013.01)

(58) Field of Classification Search
CPC ............ A61M 27/006; A61M 39/0247; A61M 2039/0276; A61M 2210/0687; A61M 2039/025; A61M 39/24
See application file for complete search history.

(56) References Cited

U.S. PATENT DOCUMENTS 3,333,588 A * 8/1967 Schulte ............... A61M 27/006
604/297
3,556,122 A * 1/1971 Laerdal ............... A61M 16/208
137/859

(Continued)

FOREIGN PATENT DOCUMENTS

JP 2014-176694 A 9/2014
KR 10-2016-0143502 A 12/2016
WO WO-0154766 A1 * 8/2001 .......... A61M 27/006

*Primary Examiner* — Leslie R Deak
(74) *Attorney, Agent, or Firm* — Hammer & Associates, P.C.

(57) ABSTRACT

The present invention provides a skull implant-type automatic fluid drain device comprising: a body having a first port to be connected to a catheter, a second port provided opposite the first port, and a flow passage connecting the first port and the second port; a separation member for separating the flow passage into first and second sub-channels; a first valve fixed to the separation member and provided to allow the movement of a fluid that moves from the first port to the second port in the first sub-channel; and a second valve fixed to the separation member and provided to allow the movement of a fluid that moves from the second port to the first port in the second sub-channel, wherein each of the first valve and the second valve has an inflow end portion that is open and a discharge end portion provided in a closed state (Continued)

such that the same is selectively opened at an allowed opening pressure or higher; each of the first valve and the second valve is configured such that the inner flow sectional area decreases along the direction of allowed movement of the fluid passing through each of the inflow end portion and the discharge end portion; and the allowed opening pressures of the first valve and the second valve are set to differ from each other.

4 Claims, 4 Drawing Sheets

(56) References Cited

U.S. PATENT DOCUMENTS

| | | | |
|---|---|---|---|
| 4,084,606 A * | 4/1978 | Mittleman | A61M 5/00 |
| | | | 137/854 |
| 4,681,559 A * | 7/1987 | Hooven | A61M 27/006 |
| | | | 604/9 |
| 4,781,673 A | 11/1988 | Watanabe | |
| 5,707,356 A * | 1/1998 | Paul | A61M 1/742 |
| | | | 604/167.03 |
| 2004/0102761 A1 | 5/2004 | Ahmed | |
| 2015/0094644 A1 * | 4/2015 | Lenihan | A61M 39/24 |
| | | | 604/9 |

* cited by examiner

SKULL IMPLANT-TYPE AUTOMATIC FLUID DRAIN DEVICE

TECHNICAL FIELD

The present invention relates to a skull implant-type automatic fluid drain device capable of not only supplying a medicine into a cerebral ventricle but also directly draining a cerebrospinal fluid from the cerebral ventricle to the outside of a body.

BACKGROUND ART

Generally, leptomeningeal carcinomatosis refers to multiple neurological symptoms caused by metastasis of malignant cells to leptomeninges and it has been reported that such leptomeningeal carcinomatosis occurs in about 3 to 8% of all solid cancers.

Leptomeningeal carcinomatosis (LMC) of solid cancer is a symptom in which cancer cells spread to a brain and an arachnoid membrane and cerebrospinal fluid of a spinal cord and occurs at a late stage of cancer, and occurrence thereof has increased recently since a survival time of cancer patients is increasing due to development in cancer treatment techniques.

LMC may occur in all types of cancers, and particularly, frequently and easily occurs in breast cancers, lung cancers, head-and-neck cancers, melanoma, and stomach cancers and has been known to occur in 4 to 15% of total cancer patients and a reported 25% of autopsy examples (U.S. National Cancer Institute (NCI)).

When prosencephalic radiation treatment is performed, a remaining life expectancy is about four months. When a palliative intrathecal anticancer medicine implant is performed, a remaining life expectancy is about six months. As described above, a prognosis is poor (Bokestein, 1998) and serious neurological symptoms such as a serious headache caused by an increase in intracranial pressure and not reacting to painkillers, vomiting, multiple cerebral nerve paralysis, clouded consciousness, and the like are accompanying such that daily life and quality of life of a patient may be very seriously degraded.

Generally, an implantable medicine-impregnating port is an apparatus developed for a patient who has an illness which needs continuous or intermittent drug delivery for a long time, the apparatus being capable of discharging a medicine injected from the outside to a designated part through a medicine discharge tube while being implanted inside a patient's body.

The implantable medicine-impregnating port is directly connected to an artery or vein through the medicine discharge tube and directly transfers the medicine injected from the outside to an inside of a blood vessel and is used for a cancer patient, particularly, anticancer medicine treatment of a brain tumor patient in addition thereto.

However, a conventional implantable medicine-impregnating port merely has a structure for anticancer medicine treatment for a brain tumor patient but is not usable for discharging a cerebrospinal fluid in a cerebral ventricle. Also, in the case of an existing Ommaya reservoir for discharging a cerebrospinal fluid, since it is impossible to fix a needle to a device, it is impossible to continuously drain a cerebrospinal fluid. Currently, in the case of a shunt system using a valve or a check valve, a method of allowing a cerebrospinal fluid to detour to another space of a human body is performed but a disadvantage such as blocking of a shunt and the like is present.

DISCLOSURE

Technical Problem

The present invention is directed to providing a cranial implant-type automatic fluid drain device capable of not only supplying a medicine into a cerebral ventricle but also directly draining a cerebrospinal fluid from the cerebral ventricle to the outside of a body.

Technical Solution

According to one aspect of the present invention, there is provided a skull implant-type automatic fluid drain device including a body including a first port configured to be connected to a catheter, a second port provided opposite the first port, and a flow path connecting the first port to the second port; a separation member configured to separate the flow path into first and second sub-flow paths; a first valve fixed to the separation member and disposed at the first sub-flow path to allow a fluid to flow from the first port to the second port; and a second valve fixed to the separation member and provided at the second sub-flow path to allow a fluid to flow from the second port to the first port. Here, the first valve and the second valve each include an opened inlet end portion and a discharge end portion provided in a closed state to be selectively opened at an opening-allowable pressure or higher and are each provided such that an internal flow sectional area decreases along a direction in which the fluid passing through each of the inlet end portion and the discharge end portion is allowed to flow. Also, the opening-allowable pressures of the first valve and the second valve are set to be different from each other.

Also, the first valve may be disposed such that the discharge end portion faces the second port, and the second valve may be disposed such that the discharge end portion faces the first port.

Also, each of the first and second valves may be configured to be opened only when a pressure applied to the discharge end portion along an inflow direction of a fluid is higher than or equal to the opening-allowable pressure.

Also, the first and second valves may each include an inclined surface formed to be inclined from the discharge end portion to the inlet end portion to prevent the fluid from flowing backward from the discharge end portion to the inlet end portion.

Also, each of the first valve and the second valve may be configured such that a flow sectional shape of the inlet end portion differs from a flow sectional shape of the discharge end portion.

Also, the second port may include a diaphragm formed of silicone to allow injecting of a medicinal fluid or draining a cerebrospinal fluid.

Also, the body may include a rib in which at least one fixing hole configured to be fixed to a cranium is formed.

Also, the opening-allowable pressure of the second valve may be a pressure at which a medicinal fluid is injected and be in a range of 10 psi to 60 psi on the basis of a 3 ml syringe.

Also, the opening-allowable pressure of the first valve may be an increase in a pressure inside the cerebral ventricle and be in a range of 10 mmHg to 30 mmHg.

According to another aspect of the present invention, there is provided a skull implant-type automatic fluid drain device kit including a syringe which injects a medicinal fluid or drains a cerebrospinal fluid outside a human body, an automatic fluid drain device, a soft catheter connected to the fluid drain device and directly connected to an inside of a cerebral ventricle, and a stiff metal wire guiding the catheter to the cerebral ventricle.

Here, the automatic fluid drain device includes a body including a first port configured to be connected to a catheter, a second port provided opposite the first port, and a flow path connecting the first port to the second port; a separation member separating the flow path into first and second sub-flow paths; a first valve fixed to the separation member and provided at the first sub-flow path to allow a fluid to flow from the first port to the second port; and a second valve fixed to the separation member and provided at the second sub-flow path to allow a fluid to flow from the second port to the first port. The first valve and the second valve each include an opened inlet end portion and a discharge end portion provided in a closed state to be selectively opened at an opening-allowable pressure or higher and are each provided such that an internal flow sectional area decreases along a direction in which the fluid passing through each of the inlet end portion and the discharge end portion is allowed to be flowed. The opening-allowable pressures of the first valve and the second valve are set to be different from each other.

Also, the first valve may be disposed such that the discharge end portion faces the second port, and the second valve may be disposed such that the discharge end portion faces the first port.

Also, each of the first and second valves may be configured to be opened only when a pressure applied to the discharge end portion along an inflow direction of a fluid is higher than or equal to the opening-allowable pressure.

Also, the second port includes a diaphragm formed of silicone to allow injecting of a medicinal fluid or draining a cerebrospinal fluid.

Advantageous Effects

According to the exemplary embodiment of the present invention, a skull implant-type automatic fluid drain device may not only supply a medicine into a cerebral ventricle but also directly drain a cerebrospinal fluid from the cerebral ventricle outside a body when a pressure inside the cerebral ventricle suddenly and abnormally increases.

Also, a medicine may be continuously injected into the cerebral ventricle, or the cerebrospinal fluid may be drained outside the body through a scalp using a syringe without a secondary operation.

MODES OF THE INVENTION

Hereinafter, exemplary embodiments of the present invention will be described in detail with reference to the attached drawings. Before this, the terms used in the specification and the claims should not be limited to general or lexical meanings and should be interpreted as meanings and concepts coinciding with the technical concept of the present invention on the basis of a principle in which the inventor can appropriately define the concept of the terms to describe the invention in the best manner.

Also, regardless of reference numerals, equal or corresponding components will be referred to with equal or similar reference numerals and a repetitive description thereof will be omitted. For convenience of description, sizes and shapes of components illustrated in the drawings may be exaggerated or reduced.

Accordingly, since embodiments disclosed in the specification and components shown in the drawings are merely exemplary embodiments of the present invention and do not represent an entirety of the technical concept of the present invention, it should be understood that a variety of equivalents and modifications capable of being substituted for the embodiments and the components may be present at the time of filing the present application.

The present invention relates to a skull implant-type automatic fluid drain device capable of not only supplying a medicine into a cerebral ventricle but also directly draining a cerebrospinal fluid from the cerebral ventricle to the outside of a body. According to an exemplary embodiment of the present invention, when a pressure in a cerebral ventricle suddenly and abnormally increases, an automatic fluid drain device may directly drain a cerebrospinal fluid from a cerebral ventricle outside a body. Also, a medicine may be continuously injected into the cerebral ventricle or the cerebrospinal fluid may be drained to the outside of the body through a scalp using a syringe without a secondary operation.

Figure 1:
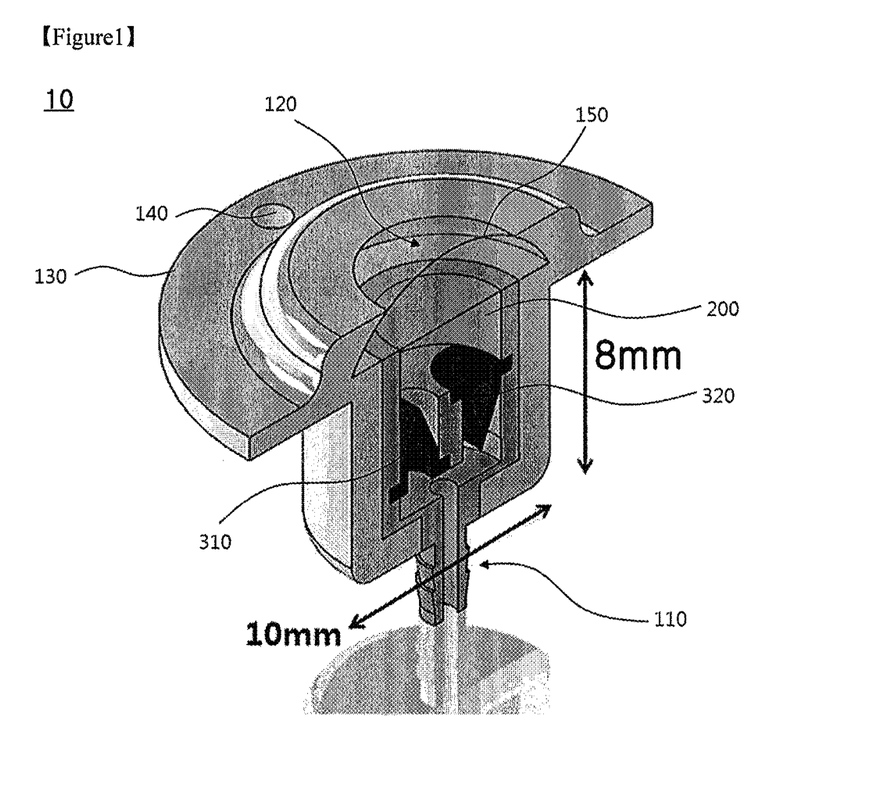
FIG. 1 is a cross-sectional perspective view of a skull implant-type automatic fluid drain device according to one embodiment of the present invention.
Figure 2:
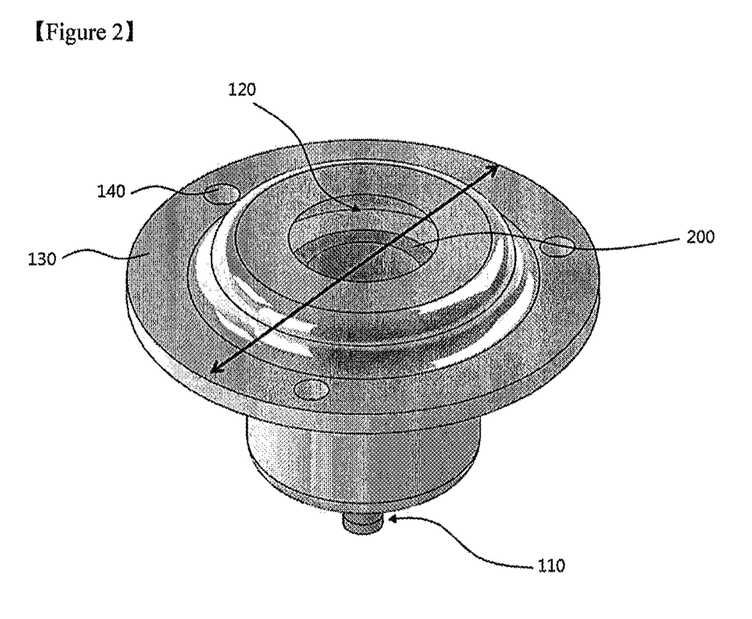
FIG. 2 is a perspective view of the skull implant-type automatic fluid drain device according to one embodiment of the present invention.
Figure 3:
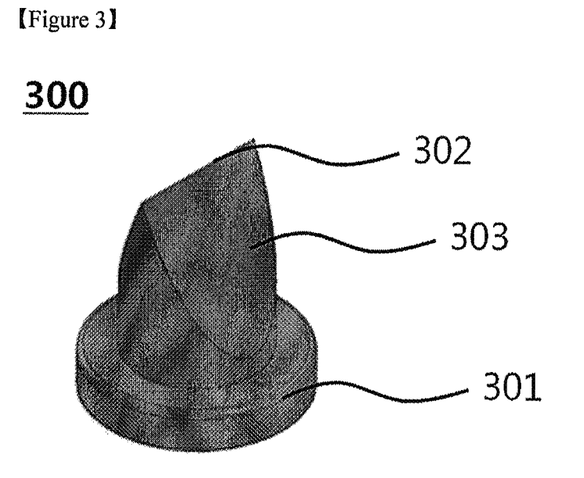
FIG. 3 is a perspective view illustrating a valve according to one embodiment of the present invention.
Figure 4:
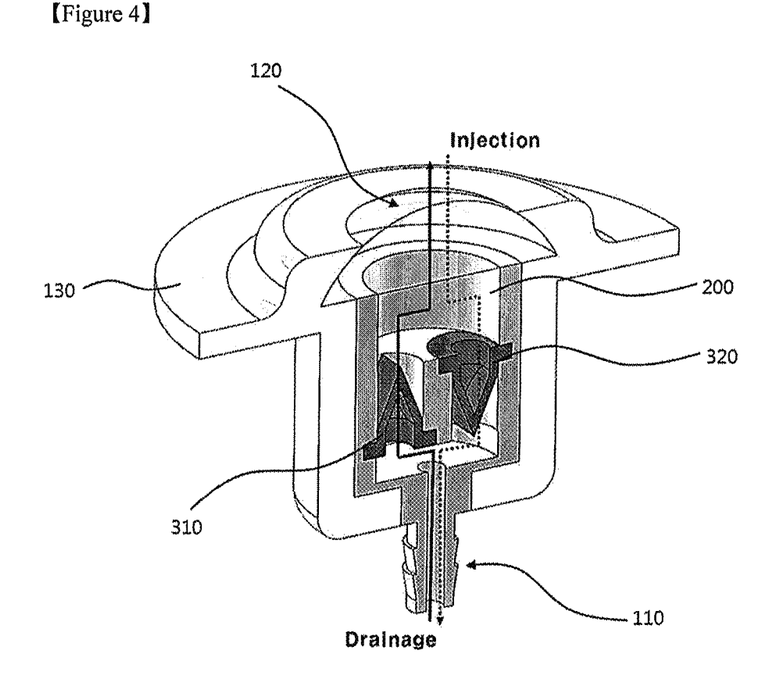
FIG. 4 is a descriptive view illustrating a state of using the automatic fluid drain device according to one embodiment of the present invention.

FIG. 1 is a cross-sectional perspective view of a skull implant-type automatic fluid drain device 10 according to an exemplary embodiment of the present invention. FIG. 2 is a perspective view of the skull implant-type automatic fluid drain device according to one embodiment of the present invention. FIG. 3 is a perspective view illustrating a valve according to one embodiment of the present invention. FIG. 4 is a view illustrating a state of using the automatic fluid drain device according to one embodiment of the present invention.

Hereinafter, with reference to FIGS. 1 to 4, the skull implant-type automatic fluid drain device and a skull implant-type automatic fluid drain device kit according to one embodiment of the present invention will be described in detail.

First, in a human skull(cranium), unlike a general form of long bones of arms and legs, hard compact bones form an exterior and cancellous bones are present between the compact bones. The skull implant-type automatic fluid drain device 10 according to the present invention may be mounted in a cranium by cutting a compact bone and a cancellous bone among three layers and forming a device insertion hole therein.

As shown in FIG. 1, the automatic fluid drain device 10 according to the present invention includes a body 100 including a first port 110 and a second port 120 and includes a separation member 200 to which a first valve 310 and a second valve 320 are fixed.

The body 100 of the present invention includes the first port 110 for connecting to a catheter, the second port 120 provided opposite the first port 110, and a flow path connecting the first port to the second port.

Also, the flow path includes the separation member 200 separating the flow path into first and second sub-flow paths, and the first valve 310 may be provided at the first sub-flow path to be fixed to the separation member 200 and to allow a fluid to flow from the first port 110 to the second port 120.

Also, the second valve 320 may be provided in the second sub-flow path to be fixed to the separation member 200 and to allow a fluid to flow from the second port 120 to the first port 110.

That is, the first and second valves may each include an inlet end portion 301 that is opened and a discharge end portion 302 provided in a closed state to be selectively opened at an opening-allowable pressure or higher.

Here, the first and second valves 310 and 320 may be check valves but are not limited thereto.

In addition thereto, each of the first valve 310 and the second valve 320 may be provided such that an internal flow sectional area thereof decreases along a direction in which the fluid is allowed to flow.

That is, they may each be provided such that the internal flow sectional area decreases along the direction in which the fluid passing through the inflow end portion and the discharge end portion of each of the first and second valves is allowed to flow.

Also, the opening allowable pressures of the first valve 310 and the second valve 320 may be set to be different from each other.

In more detail, the body 100 may be implanted by forming a hole in a patient's cranium and be located below a scalp by stitching up the scalp.

Accordingly, the body 100 may include a rib 130 in which at least one fixing hole 140 for being fixed to the cranium is formed.

Particularly, the rib 130 may be, for example, a circular shape, and any shapes having a purpose of being disposed in the cranium will do.

Also, the body 100 including the rib 130 may be formed of a bio-friendly, anticorrosive, and nonmagnetic (MRI compatible) metal and may be, for example, formed of titanium, stainless steel, or the like.

Meanwhile, the second port 120 may further include a diaphragm 150 formed of a silicone for injecting a medicine or draining a cerebrospinal fluid and be configured to seal the second port 120.

The diaphragm 150 may be formed of an elastic material such as silicone such that a syringe needle may be easily inserted in order to inject a medicine or to drain the cerebrospinal fluid from the body 100.

FIG. 3 is a view illustrating the valves 310 and 320 located inside the body 100. As shown in FIG. 3, the first and second valves 310 and 320 may be provided such that the inlet end portion 301 is opened and the discharge end portion 302 is in a closed state to be selectively opened at an opening-allowable pressure or higher.

Here, the opening-allowable pressure is a pressure at which a fluid, which has flown through the inlet end portion 301 of a valve 300, is allowed to pass through the discharge end portion 302 and means a certain pressure at which the discharge end portion is opened such that the fluid passes through the discharge end portion and is discharged.

In more detail, referring to FIG. 4 for a solid line (drainage), the opening-allowable pressure of the first valve 310 means a pressure which allows a fluid to flow from the first port into the inlet end portion of the first valve and pass through the discharge end portion of the first valve to flow from the first port to the second port, that is, a pressure for opening the discharge end portion of the first valve. When the pressure is higher than or equal to the opening-allowable pressure of the first valve, a cerebrospinal fluid inside the cerebral ventricle passes through the first valve through the first port and is discharged into the second port connected to the outside of the body.

Here, when the opening-allowable pressure of the first valve is referred to as a first pressure, the discharge end portion of the first valve is opened when a pressure thereinside is higher than or equal to the first pressure such that the fluid may flow from the first port toward the second port.

The first pressure may be preset to have a certain pressure range.

On the other hand, referring to FIG. 4 for a dotted line (injection), the opening-allowable pressure of the second valve 320 means a pressure which allows a fluid to flow from the second port into the inlet end portion of the second valve and pass through the discharge end of the second valve to flow from the second port to the first port, that is, a pressure for opening the discharge end portion of the second valve. When the pressure is higher than or equal to the opening-allowable pressure of the second valve, a medicine or medicinal fluid injected into the second port passes through the second valve through the second port and is injected into the second port connected to the inside of the cerebral ventricle.

Here, when the opening-allowable pressure of the second valve is referred to as a second pressure, the discharge end portion of the second valve is opened when a pressure thereinside is higher than or equal to the second pressure such that the fluid may move from the second port toward the first port.

The second pressure may be preset to have a certain pressure range.

The first and second valves 310 and 320 are valve systems opened only in a single direction when the pressure thereinside is higher than or equal to the preset pressure. When the pressures thereinside increase to be higher than or equal to the preset pressures, the first and second valves 310 and 320 are automatically opened such that the medicinal fluid may be injected into the cerebral ventricle or the cerebrospinal fluid inside the cerebral ventricle may be discharged while passing through the separation member 200.

In more detail, when a fluid flows through the valve 300, the discharge end portion 302 is opened at the opening-allowable pressure or higher such that the fluid may flow from the inlet end portion 301 to the discharge end portion 302.

Also, an inclined surface 303 formed to be inclined from the discharge end portion 302 to the inlet end portion 301 may prevent the fluid from flowing backward from the discharge end portion 302 to the inlet end portion 301.

As an example, when a medicinal fluid is injected through the second port 120, the injected medicinal fluid may pass through the second valve 320 and flow toward the first port 110.

Also, the medicinal fluid flows along the inclined surface 303 of the first valve such that the medicinal fluid is injected into the cerebral ventricle only through the second valve 320.

That is, the first valve 310 may be disposed to allow the discharge end portion 302 to face the second port 120, and the second valve 320 may be disposed to allow the discharge end portion 302 to face the first port 110.

Accordingly, each of the first and second valves may be configured to be opened only when a pressure applied to the discharge end portion along an inflow direction of a fluid is higher than or equal to the opening-allowable pressure.

FIG. 4 is a descriptive view illustrating a state of using the automatic fluid drain device 10 according to the present invention. The state of using the automatic fluid drain device 10 will be described in detail with reference to the drawing.

First, in the case of automatic draining of a cerebrospinal fluid to decrease a pressure inside a cerebral ventricle of a patient, while the automatic fluid drain device 10 is implanted into a cranium, when the pressure inside the cerebral ventricle of the patient abnormally increases, a cerebrospinal fluid inside the cerebral ventricle flows toward the inlet end portion 301 of the first port 110 through a catheter (not shown) connected to the inside of the cerebral ventricle of the patient and the discharge end portion 302 of the first port 110 is opened by a pressure generated by the movement of the cerebrospinal fluid such that the cerebrospinal fluid may flow to the separation member 200.

The cerebrospinal fluid which has passed through the separation member 200 may be drained to the outside of a body using a syringe needle passing through the diaphragm 150 of the second port 120 such that excessive pressure inside the cerebral ventricle of the patient may be decreased.

Here, the opening-allowable pressure of the first valve 310 is an increase in the pressure inside the cerebral ventricle and may be in a range of 10 mmHg (0.193 psi) to 60 mmHg (1.16 psi) and more particularly may be in a range of 10 mmHg (0.193 psi) to 30 mmHg (0.58 psi).

That is, the first pressure may be in a range of 10 mmHg (0.193 psi) to 60 mmHg (1.16 psi), and more particularly, may be in a range of 10 mmHg (0.193 psi) to 30 mmHg (0.58 psi).

Particularly, the increase in the pressure inside the cerebral ventricle differs for each patient, and the device may be manufactured to be within a pressure range set corresponding to a pressure range of a patient. That is, a plurality of devices may be manufactured by dividing the pressure range into a plurality of regions corresponding to a range of the increased pressure inside the cerebral ventricle of the patient.

As described above, since a pressure inside a cerebral ventricle differs for each patient, the opening-allowable pressure of the first valve 310 may be set corresponding to each patient to drain a cerebrospinal fluid.

On the other hand, in the case of injecting a medicinal fluid into a cerebral ventricle of a patient, a syringe needle passes through the diaphragm 150 of the second port 120 and the medicinal fluid is injected.

The discharge end portion 302 of the second valve 320, which is provided in a closed state, is opened by a pressure generated when the injected medicinal fluid is injected while passing through the separation member 200 such that the medicinal fluid flows toward the first port 110.

The catheter (not shown) connected to the first port 110 is connected to the inside of the cerebral ventricle of the patient such that the medicinal fluid may be injected into the cerebral ventricle of the patient through the catheter.

Here, the catheter may mean a kind of a tube, and any catheters used in the art to inject a medicinal fluid are usable.

Particularly, the opening-allowable pressure of the second valve 320 is a pressure at which a medicinal fluid is injected and may be in a range of 10 psi (517 mmHg) to 60 psi (3,103 mmHg).

That is, the second pressure may be in a range of 10 psi to 60 psi.

Here, the medicinal fluid injection pressure may be based on a 3 ml syringe.

A difference in the opening-allowable pressure is generated since a pressure of injecting a medicinal fluid using a syringe differs from an increased pressure inside a cerebral ventricle. Since the pressure of injecting the medicinal fluid is generated to be higher than the increased pressure inside the cerebral ventricle, it is necessary to provide the first valve 310 and the second valve 320 which have different pressures.

That is, the first pressure and the second pressure may be set to be different from each other, and the second pressure has a higher pressure range than that of the first pressure.

As described above, due to the first and second valves having different opening-allowable pressures, even when the cerebrospinal fluid discharged from the cerebral ventricle is discharged through the first valve and flows toward the second valve through the separation member, a pressure of the fluid which has flowed is not higher than or equal to the opening-allowable pressure of the second valve such that there is present an effect in which the fluid does not flow backward into the cerebral ventricle.

On the other hand, even when a medicinal fluid injected through the second port is flowed toward the first valve through the separation member, the medicinal fluid flows along the inclined surface 303 of the first valve such that there is present an effect that the medicinal fluid is injectable into a cerebral ventricle only through the second valve.

Meanwhile, referring to FIG. 3, each of the first valve 310 and the second valve 320 may be provided such that an internal flow sectional area thereof decreases in a direction in which the fluid passing through each of the valve is allowed to flow.

Particularly, the first valve 310 and the second valve 320 may be provided such that a flow sectional shape of the inlet end portion differs from a flow sectional shape of the discharge end portion.

In more detail, since the inlet end portion 301 of each of the first and second valves may have a circular sectional shape and the discharge end portion 302 has a different shape having a cross section smaller than that of the inlet end portion 301 due to the inclined surface 303 formed from the inlet end portion 301 to the discharge end portion 302, an internal flow section decreases along a direction of a fluid flowing from the inlet end portion toward the discharge end portion is allowed to flow such that the flow sectional shape of the inlet end portion may differ from the flow sectional shape of the discharge end portion.

Meanwhile, referring to FIGS. 1 and 2, a diameter of a bottom of the body 100 including the separation member 200 provided at the first port 110 of the automatic fluid drain device 10 according to the present invention may adequately be in a range of 8 mm to 10 mm.

Also, a height of the body 100 including the separation member 200 may adequately be in a range of 6 mm to 8 mm.

In addition, a diameter of a top of the body 100 including the rib 130 is adequately in a range of 18 mm to 20 mm.

As an example, when the diameter of the bottom of the body 100 is less than 8 mm and the height of the body 100 is less than 6 mm, an internal space may be slightly decreased such that a space configured to allow injecting of a medicinal fluid may be insufficient. When the diameter of the bottom of the body 100 is greater than 10 mm, a space necessary for inserting the body 100 into a cranium increases more than is needed. Accordingly, since it is necessary to bore and remove a larger area of the cranium, a patient may be harmed more than is necessary and an operational time also increases to have a negative effect on the patient.

Also, when the height of the body 100 is greater than 8 mm, the top of the body 100 may protrude to be higher than a skull surface after the body is inserted into the cranium such that it is inefficient for stitching up a scalp. Also, due to a contact with the outside after an operation, an inner wall of the scalp may be damaged or an exterior does not look excellent.

Also, the diameter of the top of the body 100 including the rib 130 may be in a range of 18 mm to 20 mm but is not limited thereto.

A conventional shunt system with respect to a cerebrospinal fluid maintains an intracranial pressure at a certain level by discharging an excessive cerebrospinal fluid into an abdominal cavity and a peritoneal cavity of a human body in real time such that a pain of a patient is relieved relatively quickly.

However, the shunt system has a limitation of having no function of injecting a medicinal fluid and has disadvantages in which meningitis, ventriculitis, peritonitis, septicaemia, endocarditis, and the like may occur to a patient due to shunt infection caused by a blockage of the shunt. Also, when a slight cerebral shock occurs, bleeding generated by the shock may not stop such that severe side effects may be caused to the patient.

Accordingly, the present invention may solve problems of related arts described above by directly draining a cerebrospinal fluid outside in addition to injecting of a medicinal fluid.

The present invention provides a skull implant-type automatic fluid drain device kit.

For example, the automatic fluid drain device kit relates to a device kit which includes the above-described skull implant-type automatic fluid drain device and is needed for injecting a medicinal fluid or for automatically draining a cerebrospinal fluid. Accordingly, as details with respect to the automatic fluid drain device kit, which will be described below, the above description with respect to the automatic fluid drain device may be equally applied thereto.

A skull implant-type automatic fluid drain device kit according to an exemplary embodiment of the present invention includes a syringe for injecting a medicinal fluid or draining a cerebrospinal fluid outside a human body, an automatic fluid drain device, a soft catheter connected to the fluid drain device and directly connected to an inside of a cerebral ventricle, and a stiff metal wire guiding the catheter to the cerebral ventricle.

Here, the automatic fluid drain device includes a body including a first port for being connected to a catheter, a second port provided opposite the first port, and a flow path connecting the first port to the second port; a separation member separating the flow path into first and second sub-flow paths; a first valve fixed to the separation member and provided at the first sub-flow path to allow a fluid to flow from the first port to the second port; and a second valve fixed to the separation member and provided at the second sub-flow path to allow a fluid to flow from the second port to the first port. The first valve and the second valve each include an opened inlet end portion and a discharge end portion provided in a closed state to be selectively opened at an opening-allowable pressure or higher and are each provided such that an internal flow sectional area decreases along a direction in which the fluid passing through each of the inlet end portion and the discharge end portion is allowed to flow. The opening-allowable pressures of the first valve and the second valve are set to be different from each other.

Also, the first valve may be disposed such that the discharge end portion faces the second port, and the second valve may be disposed such that the discharge end portion faces the first port.

Also, each of the first and second valves may be configured to be opened only when a pressure applied to the discharge end portion along an inflow direction of a fluid is higher than or equal to the opening-allowable pressure.

Also, the second port includes a diaphragm formed of silicone for injecting a medicinal fluid or draining a cerebrospinal fluid.

The automatic fluid drain device kit includes a syringe for injecting the medicinal fluid or draining the cerebrospinal fluid outside through the automatic fluid drain device 10.

Here, in addition to the syringe, any devices, to which a needle capable of being stuck into the silicone diaphragm 150 of the second port 120 to inject a medicinal fluid or to drain a cerebrospinal fluid outside through the automatic fluid drain device 10 is connected, may be used.

Also, the automatic fluid drain device 10 may be provided to which a needle capable of being stuck to the diaphragm 150 formed of silicone is connected.

Also, a soft catheter connected to the automatic fluid drain device and directly connected to the inside of the cerebral ventricle is included.

Here, the catheter has a soft material having a pipe shape.

Also, a stiff metal wire guiding the catheter to the cerebral ventricle is included.

Particularly, the wire is usable while being stuck into the soft catheter.

The catheter is changed to have a hard property by the wire.

Accordingly, a clinician may directly grip the catheter with a hand and press in, disconnect, and bore through relatively soft cerebral tissues such that an end of the catheter may reach the inside of the cerebral ventricle.

That is, the wire may be a stiff metal wire.

Since the catheter is formed of a soft material such as a silicone rubber and the like and is difficult to directly insert into the cerebral ventricle, the kit may include a stiff metal wire to insert the catheter into the cerebral ventricle.

Accordingly, it is possible to insert the catheter into the cerebral ventricle by using the stiff metal wire.

The invention claimed is:

1. A skull implant-type automatic fluid drain device comprising:
a body comprising a first port configured to be connected to a catheter, a second port provided opposite the first port, and a flow path connecting the first port to the second port;
a separation member configured to separate the flow path into a first sub-flow path and a second sub-flow path;
a first valve fixed to the separation member and disposed at the first sub-flow path to allow a fluid to flow from the first port to the second port; and
a second valve fixed to the separation member and provided at the second sub-flow path to allow a fluid to flow from the second port to the first port,
wherein the first valve and the second valve each comprise an opened inlet end portion and a discharge end portion provided in a closed state to be selectively opened at an opening-allowable pressure or higher and are each provided such that an internal flow sectional area decreases along a direction in which the fluid passing through each of the inlet end portion and the discharge end portion is allowed to flow,
wherein the opening-allowable pressures of the first valve and the second valve are set to be different from each other,
wherein the first and second valves each comprise an inclined surface formed to be inclined from the discharge end portion to the inlet end portion to prevent the fluid from flowing backward from the discharge end portion to the inlet end portion, wherein each of the first valve and the second valve is configured such that a flow sectional shape of the inlet end portion differs from a flow sectional shape of the discharge end portion, wherein the second port comprises a diaphragm formed of silicone and configured to allow injecting of a medicinal fluid or draining of a cerebrospinal fluid, wherein the opening-allowable pressure of the second valve is a pressure at which a medicinal fluid is injected and is in a range of 10 psi to 60 psi on the basis of a 3 ml syringe, and wherein the opening-allowable pressure of the first valve is a pressure being increased inside the cerebral ventricle and is in a range of 10 mmHg to 30 mmHg.

2. The skull implant-type automatic fluid drain device of claim 1, wherein the first valve is disposed such that the discharge end portion faces the second port, and wherein the second valve is disposed such that the discharge end portion faces the first port.

3. The skull implant-type automatic fluid drain device of claim 1, wherein each of the first and second valves is provided to be opened only when a pressure applied to the discharge end portion along an inflow direction of the fluid is higher than or equal to the opening-allowable pressure.

4. The skull implant-type automatic fluid drain device of claim 1, wherein the body comprises a rib in which at least one fixing hole configured to be fixed to a cranium is formed.

\* \* \* \* \*